(12) United States Patent
Schwab

(10) Patent No.: US 7,942,902 B2
(45) Date of Patent: May 17, 2011

(54) BONE ANCHOR AND SPINAL ALIGNMENT SYSTEM

(75) Inventor: Frank Johann Schwab, New York, NY (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 360 days.

(21) Appl. No.: 11/941,242

(22) Filed: Nov. 16, 2007

(65) Prior Publication Data

US 2009/0131982 A1 May 21, 2009

(51) Int. Cl.
*A61B 17/70* (2006.01)
(52) U.S. Cl. .................. 606/250; 606/251; 606/252
(58) Field of Classification Search .................. 606/246, 606/264–267, 278–279, 61, 250–253, 300–321
See application file for complete search history.

(56) References Cited

U.S. PATENT DOCUMENTS

| 5,899,903 | A | 5/1999 | Cotrel |
| 6,811,567 | B2 | 11/2004 | Reiley |
| 2002/0035365 | A1 | 3/2002 | Kumar et al. |
| 2004/0111088 | A1 | 6/2004 | Picetti et al. |
| 2005/0277920 | A1* | 12/2005 | Slivka et al. ............... 606/61 |
| 2008/0177323 | A1* | 7/2008 | Null et al. ................. 606/267 |
| 2008/0262546 | A1* | 10/2008 | Calvosa et al. ............ 606/250 |

OTHER PUBLICATIONS

European Patent Office, PCT/US2008/083312 Written Opinion of the International Searching Authority, Feb. 27, 2009, 6 pages, Europe.
European Patent Office, PCT/US2008/083312 Written Opinion of the International Report Feb. 27, 2009, 7 pages, Europe.

* cited by examiner

*Primary Examiner* — Eduardo C Robert
*Assistant Examiner* — Christina Negrelli

(57) ABSTRACT

An anchor for attaching an elongate member to bone. The anchor includes a longitudinal shaft having a tip at one end adapted to enter bone. A thread extends along the shaft for advancing the shaft into the bone and holding the shaft in place in the bone. A head is mounted on the shaft at a position spaced from the tip. The anchor also includes connector mounts spaced along the head. Each mount is adapted to connect the elongate member to the head.

33 Claims, 4 Drawing Sheets

BONE ANCHOR AND SPINAL ALIGNMENT SYSTEM

BACKGROUND

This invention generally relates to a method and apparatus for changing spinal alignment to treat spinal column deformity.

Human spines are formed from vertebrae spaced by intervertebral discs arranged in a gently curving column. Viewed from the side, the column has several curves defining different regions of the spine. Abnormal spinal curvatures occasionally occur in individuals. These abnormal curvatures of the spine include scoliosis (lateral curvature), kyphosis (exaggerated curvature usually in an upper portion of the spine), lordosis (exaggerated curvature usually in a lower portion of the spine), and combinations of these conditions. Although these abnormal curvatures may be cosmetically undesirable, in some cases they can lead to organ problems, reduce mobility of the individual and cause significant pain. Thus, correction of the abnormal spinal curvatures is frequently desirable.

Spinal column deformities are treated with a variety of approaches. In some cases, spinal implants are used to rigidly fix the vertebrae relative to one another. When the vertebrae are held in a rigid position and bone graft material is added, the vertebrae fuse leading to loss of spinal mobility and potentially accelerating degeneration of areas of the spine adjacent the fused portion. Thus, fusion is undesirable in many cases, and there is a need for a method and apparatus for correcting abnormal spinal curvatures without fusing vertebrae.

Because the abnormally curved spines can be out of alignment laterally, as well as forward and rearward, there is a need for a method and apparatus enabling surgeons to modify spinal column alignment simultaneously in multiple directions. Most conventional methods for treating spinal column deformities without fusion are only capable of correcting alignment in one direction at a time. Further, it is generally recognized that corrective methods and apparatus should be minimally invasive to reduce an opportunity for complications during and following the procedures, and to reduce healing times. In addition, there is a need for a method and apparatus allowing progressive adjustment of vertebrae to obtain a desirable optimal alignment of the spinal column for the patient.

BRIEF SUMMARY

The present invention relates to an anchor for attaching an elongate member to bone. The anchor comprises a longitudinal shaft having a tip at one end adapted to enter bone. A thread extends along the shaft for advancing the shaft into the bone and holding the shaft in place in the bone. The anchor also includes a head mounted on the shaft at a position spaced from the tip. Further, the anchor comprises a plurality of connector mounts spaced along the head. Each of the mounts is adapted to connect the elongate member to the head.

The invention also relates to a system for changing alignment of vertebrae of a spinal column. The system comprises a plurality of elongate members. Each of the members has a length sufficient to span at least one pair of vertebrae in the spinal column. In addition, the system includes a plurality of anchors. Each anchor includes an elongate threaded shaft having a tip at one end adapted to enter bone and a head on the shaft at a position spaced from the tip. The head has a plurality of connector mounts spaced along the head. Each mount is adapted to connect one of the elongate members to the head.

In yet another aspect, the invention includes a system for changing alignment of vertebrae of a spinal column. The system comprises a plurality of elongate members. Each of the members has a length sufficient to span at least one pair of vertebrae in the spinal column. The plurality of elongate members includes a first member having a first stiffness and a second member having a second stiffness greater than the first stiffness. Further, the system includes a plurality of anchors. Each anchor includes a head having a plurality of connector mounts spaced along the head. Each mount is adapted to connect one of the elongate members to the head.

Still further, the invention includes a system for changing alignment of vertebrae of a spinal column. The system comprises a plurality of elongate rods. Each rod has a length sufficient to span at least one pair of vertebrae in the spinal column. The system also comprises a plurality of anchors. Each anchor includes a head having a plurality of connector mounts spaced along the head. Each mount is adapted to connect one of the rods to the head.

In a further aspect, the invention includes a method of changing alignment of vertebrae of a spinal column. A first anchor is attached to an upper vertebra and a second anchor is attached to a lower vertebra. At least two rigid rods are connected to both the first anchor and the second anchor so each of the rods spans between the upper vertebra and the lower vertebra.

Moreover, the invention includes a method of changing alignment of vertebrae of a spinal column in which a first anchor is attached to an upper vertebra and a second anchor is attached to a lower vertebra. A rod is connected to both the first anchor and the second anchor so the rod spans between the upper vertebra and the lower vertebra. A flexible tether is connected to both the first anchor and the second anchor so the tether spans between the upper vertebra and the lower vertebra.

Other aspects of the present invention will be in part apparent and in part pointed out hereinafter.

BRIEF DESCRIPTION OF THE DRAWINGS

Corresponding reference characters indicate corresponding parts throughout the several views of the drawings.

DETAILED DESCRIPTION

Figure 1:
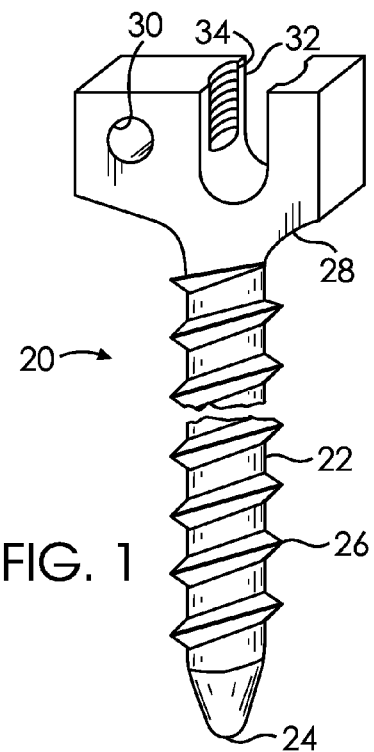
FIG. 1 is a perspective of an anchor of a first embodiment of the present invention.

Referring now to the drawings and in particular FIG. 1, an anchor of one embodiment of the present invention is designated in its entirety by the reference numeral 20. The anchor 20 is used to attach an elongate member (e.g., a metal rod) to bone.

The anchor 20 generally comprises a longitudinal shaft 22 having a tip 24 at one end adapted to enter bone. In one embodiment, the tip 24 is rounded to prevent inadvertent damage to tissue as the anchor 20 is being installed in the bone. A screw thread 26 extends along the shaft 22 for advancing the shaft into the bone and holding the shaft in place in the bone. As shown in FIG. 1, in one embodiment the screw thread 26 is a substantially uninterrupted helical thread wrapping around the shaft 22 along its entire length. The thread may have any conventional form, particularly those commonly used for bone anchor applications. The anchor 20 also includes a head 28 mounted on the shaft 22 at a position spaced from the tip 24. Two connector mounts 30, 32 are spaced laterally with respect to each other on the head 28. Each of the mounts 30, 32 is adapted to connect the elongate member to the head 28 as will be described in further detail below. As will be appreciated by those skilled in the art, the head 28 may have more than two mounts without departing from the scope of the present invention.

As further illustrated in FIG. 1, each of the mounts 30, 32 comprises an opening extending through the head 28. One mount 30 includes a circular hole extending through the head 28, and the other mount 32 includes a U-shaped channel extending through the head. As will be appreciated by those skilled in the art, the mounts may have shapes other than a hole or channel without departing from the scope of the present invention.

Although the shaft 22 may have other dimensions without departing from the scope of the present invention, in one embodiment the shaft has a length of between about 20 millimeters (mm) and about 65 mm, and a diameter of between about 3.5 mm and about 7 mm. Shafts 22 having dimensions in these ranges have been found to be particularly desirable for anchoring elongate members to a vertebra by screwing the anchors lengthwise into a pedicle of the vertebra. Further, although the anchor 20 may be made of other materials without departing from the scope of the present invention, in one embodiment the anchor is made of metal such as titanium or stainless steel. Although the anchor 20 may be made by other processes without departing from the scope of the present invention, in one embodiment the anchor is made by machining a metal or synthetic polymer.

Figure 2:
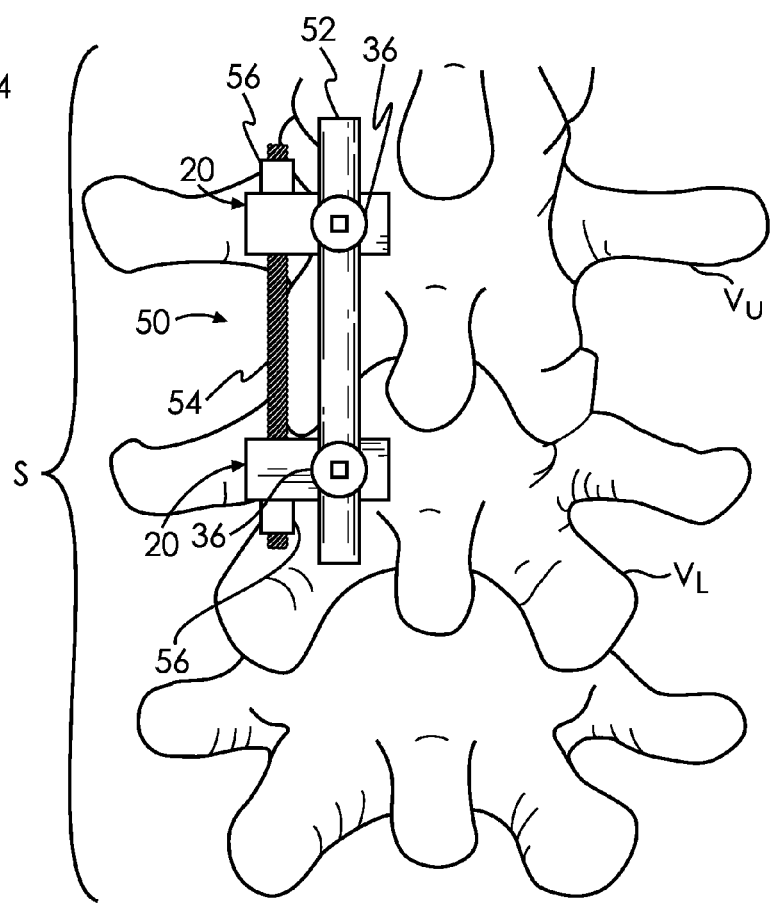
FIG. 2 is a rear elevation of a portion of a spinal column having a system of a first embodiment of the present invention.

The anchor 20 may include or work in combination with a fastener for fastening the corresponding elongate member to the head 28. In some embodiments, the fasteners are operatively connected to the mount. For example, the opposing walls of the mount 32 include threading 34 for receiving a conventional set screw 36 as shown in FIG. 2. The screw 36 may be turned to clamp an elongate member in place in the mount 32. In another alternative, the mount 30 may be used in combination with a clamp such as a conventional wire clamp. In one embodiment the wire clamp comprises a deformable sleeve or collar that may be swaged in place as will be described in further detail below. An elongate member may be inserted into the connector mount 30 and held in position with a clamp attached to the member.

Figure 3:
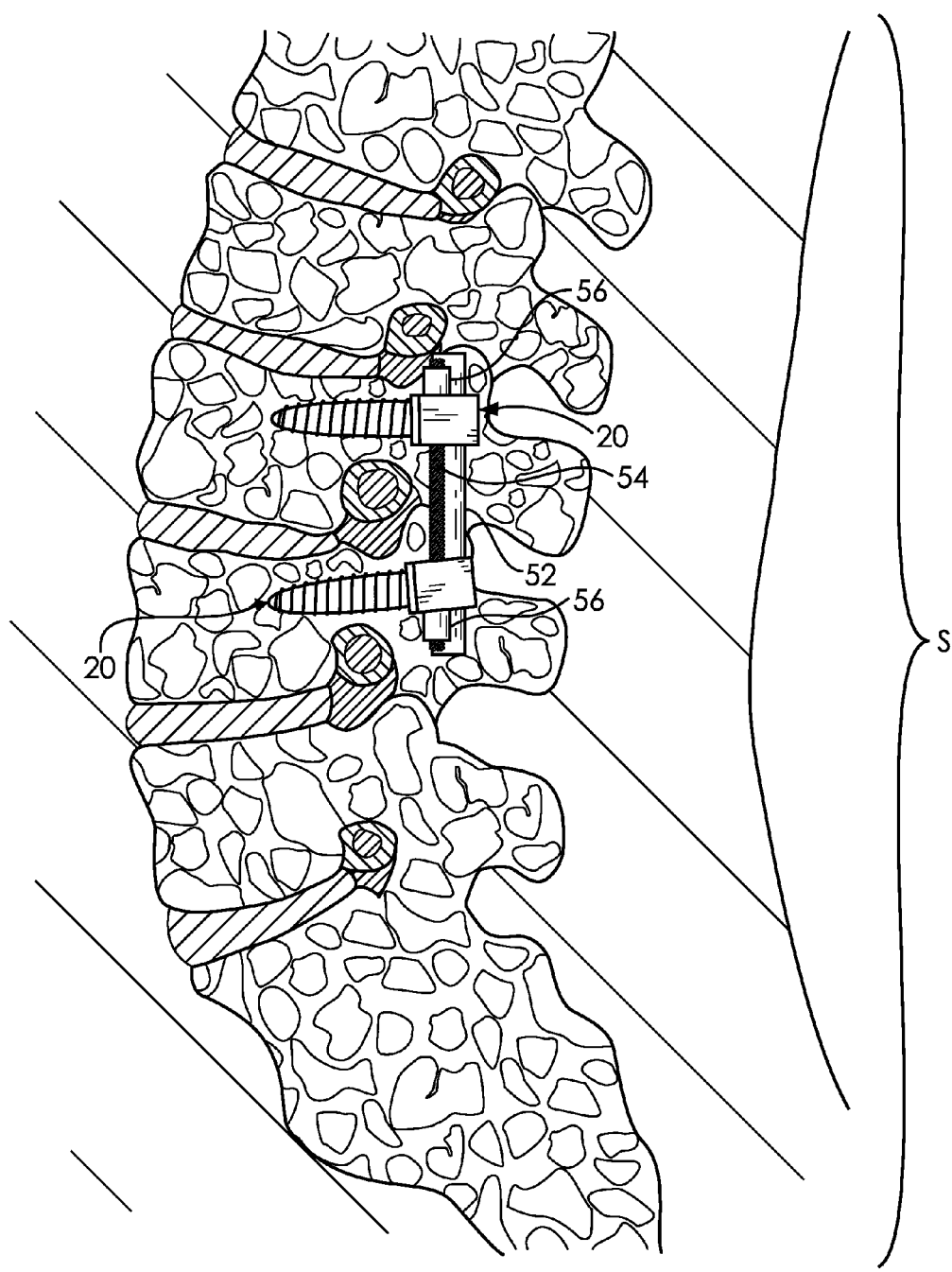
FIG. 3 is a side elevation of the portion of the spinal column having the system of the first embodiment of the present invention.

FIGS. 2 and 3 illustrate a system, generally designated by 50, incorporating the anchor 20 of the first embodiment. The system 50 is used to change relative alignment of vertebrae (e.g., upper vertebra $V_U$ and lower vertebra $V_L$ of a spinal column, generally designated by S). The system 50 includes two elongate members 52, 54. In the illustrated embodiment, the first elongate member 52 is a rigid rod having a generally circular cross section, and the second elongate member 54 is a flexible tether. In the illustrated embodiment, the flexible tether 54 is a twisted cable, however those skilled in the art will appreciate that the tether may comprise a wire, a braided cable, a natural or synthetic filament or fiber, a band, a mesh sheet, a natural or synthetic ligament, and/or a tendon. Each of the members 52, 54 has a length L sufficient to span at least one pair of vertebrae $V_U$, $V_L$ in the spinal column S. Although the members 52, 54 span only two vertebrae $V_U$, $V_L$ in the illustrated embodiment, those skilled in the art will appreciate that the members may span three or more vertebrae without departing from the scope of the present invention. Both of the members 52, 54 may be made of any suitable biocompatible material(s) having sufficient strength to avoid failure and to position the vertebrae as desired or permit change in alignment with vertebral growth. For example, in one embodiment the member 52 is made of stainless steel or titanium and member 54 is made of polyester braided material strands. Further, in this embodiment, the member 52 has a length of between about 20 mm and about 250 mm, and a diameter of between about 3 mm and about 8 mm. The member 54 of this embodiment has a length of between about 20 mm and about 250 mm, and a diameter of between about 3 mm and about 8 mm. As in many embodiments of the present invention, the member 52 has a tensile stiffness, a compressive stiffness and a bending stiffness selected to limit movement between the vertebrae $V_U$, $V_L$, and the member 54 has a bending stiffness selected to permit substantially free movement between the vertebrae in one or more directions. The member 54 has a relatively high tensile stiffness to limit movement between the vertebrae that would result in an increase in distance between them. As it has been found that bone and tissue growth are stimulated by allowing limited loading and relative movement, those skilled in the art will appreciate that when the stiffnesses of the members 52, 54 are selected appropriately, bone and/or tissue growth may be stimulated thereby reducing recovery time and post operative therapy needs.

The system 50 also includes two anchors 20. A first anchor 20 (e.g., an upper anchor) is mounted on an upper vertebra $V_U$ and a lower anchor (e.g., a lower anchor) is mounted on a lower vertebra $V_L$. As will be appreciated by those skilled in the art, more than two anchors may be used to attach a single elongate member (e.g., member 54) to multiple vertebrae or more than one anchor may be used to attach an elongate member in more than one place on a single vertebra. Although the anchors 20 shown in FIGS. 2 and 3 are anchors of the first embodiment described above, those skilled in the art will appreciate that the anchors may have other configurations including those described below without departing from the scope of the present invention.

As further illustrated in FIGS. 2 and 3, the system 50 may include a fastener such as the conventional set screw 36 described above operatively connected to at least one of the connector mounts (e.g., mount 32) for fastening the corresponding elongate member (e.g., member 52) to the head 28. In addition, the system 50 may include a clamp 56 such as the sleeve connected to at least one of the elongate members (e.g., member 54) to limit motion between the member and the head of the anchor 20. To apply the clamp 56 of the illustrated embodiment to the elongate member 54, the member is inserted into an opening in the sleeve. Once the sleeve is in position, it is swaged (i.e., deformed) to lock it in place on the member 54. As will be appreciated by those skilled in the art, the mount 32 used with the set screw 36 can permit sliding and/or rotation when partially tightened, or completely limit motion when fully tightened between the corresponding elongate member 52 and the anchor 20 in one or more planes.

Figure 4:
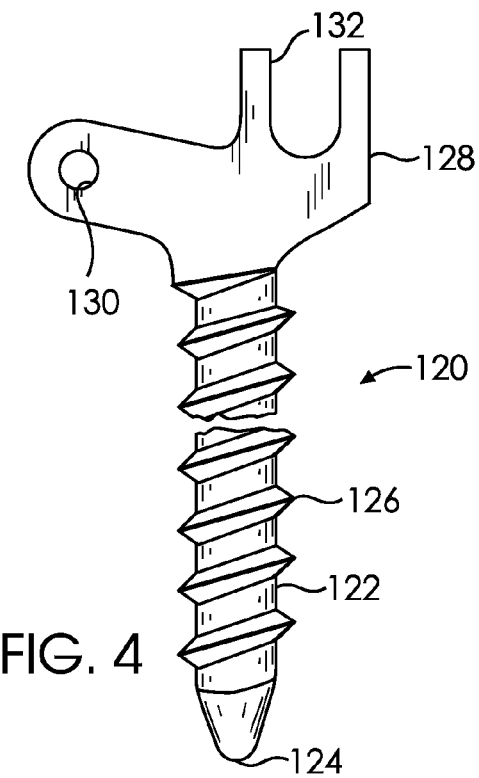
FIG. 4 is a side elevation of an anchor of a second embodiment of the present invention.
Figure 5:
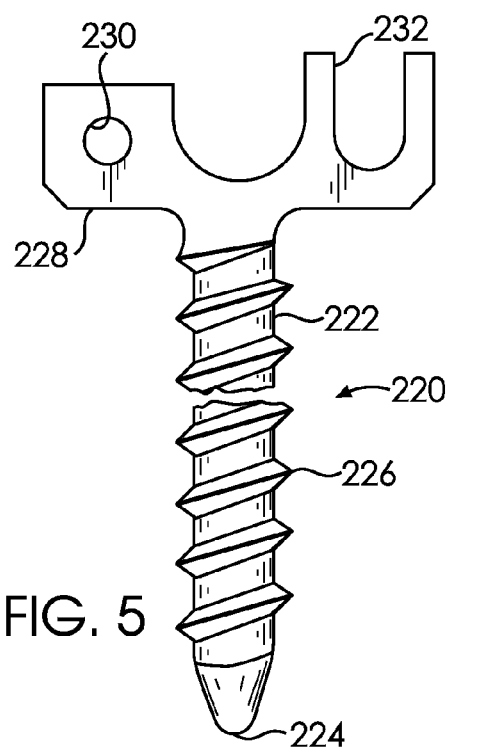
FIG. 5 is a side elevation of an anchor of a third embodiment of the present invention.
Figure 6:
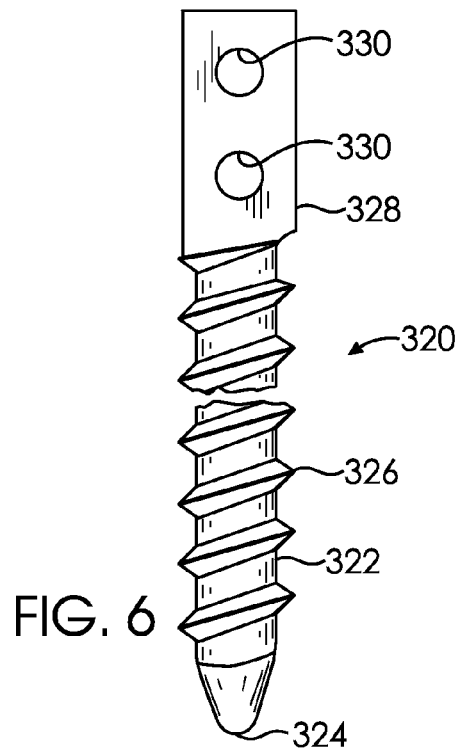
FIG. 6 is a side elevation of an anchor of a forth embodiment of the present invention.

FIGS. 4-6 illustrate alternative designs for anchors, generally designated 120, 220, 320, respectively. As these anchors 120, 220, 320 have generally similar features to the anchor 20 of the first embodiment, they will not be described in detail. Rather, the similar features of the anchors 120, 220, 320 will be identified by similar reference numbers as used for the anchor 20 incremented by 100, 200 and 300, respectively. As illustrated in FIGS. 4 and 5, the anchors 120, 220 of the second and third embodiments have mounts 130, 132 and 230, 232 that are spaced laterally with respect to each other on the heads 128 and 228. The mounts 130, 132 of the anchor 120 of the second embodiment are also spaced longitudinally, as are the mounts 330, 332 of the anchor 320 of the fourth embodiment. In both anchors 120, 220, the mounts 130, 132 and 230, 232 are spaced laterally farther apart than the mounts 30, 32 of the anchor 20. As will be appreciated by those skilled in the art, the various anchor configurations will have particular advantages when addressing particular spinal deformities.

Figure 7:
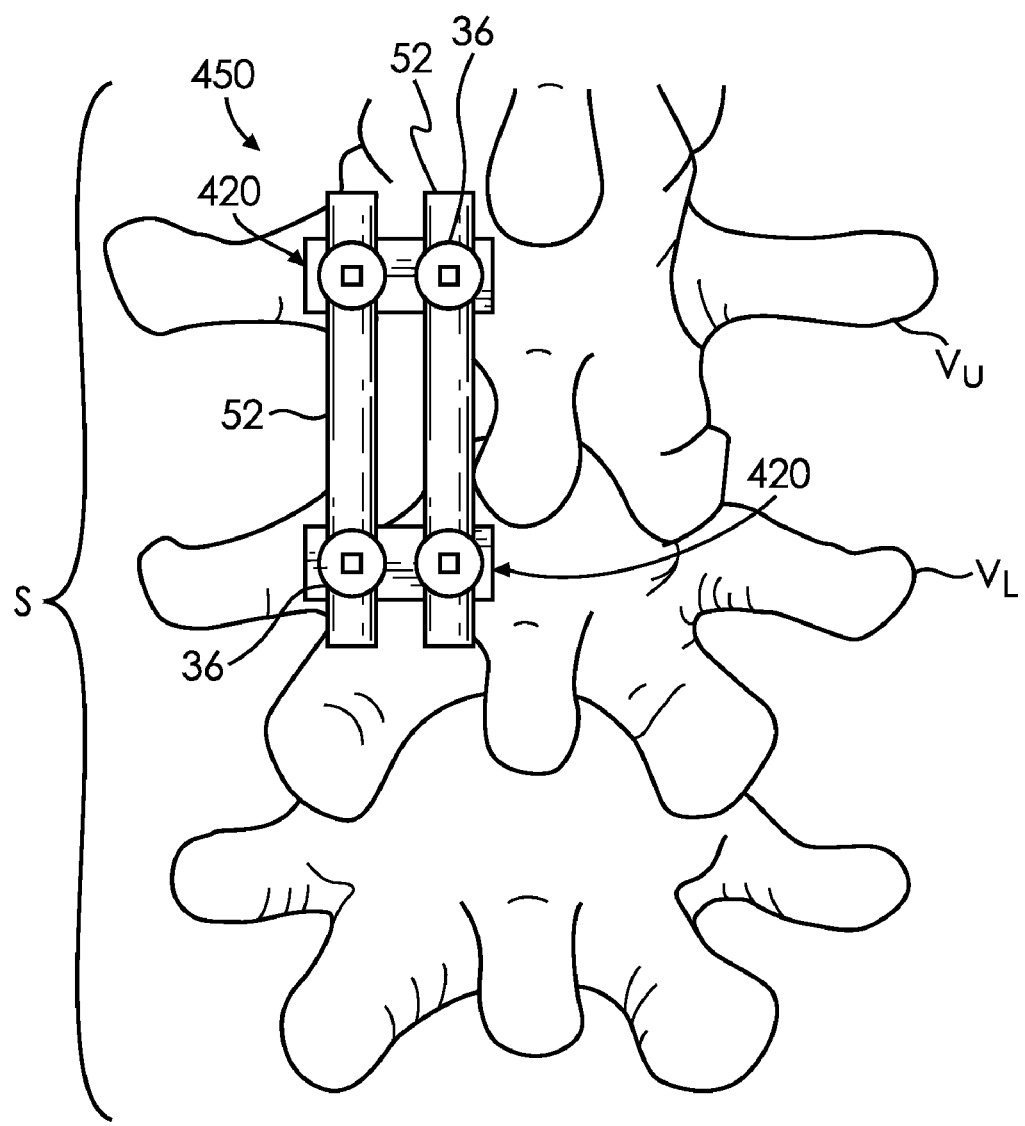
FIG. 7 is a rear elevation of a portion of a spinal column having a system of a second embodiment of the present invention.

In addition, those skilled in the art will appreciate that different mounts may be used other than those described above. Further, different combinations and types of elongate members may be used without departing from the scope of the present invention. For example, one contemplated embodiment of a system of the present invention is illustrated in FIG. 7 and designated in its entirety by the reference number 450. This embodiment includes two rigid rods 52 mounted on two anchors, generally designated by 420. It is further contemplated that these rods may have identical bending properties or difference bending properties from each other.

As will be appreciated by those skilled in the art, the anchors and systems described above may be used to change alignment of vertebrae of a spinal column. One method of use includes attaching a first anchor to an upper vertebra and attaching a second anchor to a lower vertebra using standard surgical procedures. For example, a pilot hole may be bored or drilled in the vertebra. The anchors may be threaded into the pilot hole using a wrench. Two or more rigid rods are connected to both the first anchor and the second anchor so each of the rods spans between the upper vertebra and the lower vertebra. Although the rods span adjacent vertebrae in one embodiment, it is contemplated that the rods may span and be connected to non-adjacent vertebrae. It is further contemplated that the more than two anchors and/or more than two rods may be used with this method.

In another embodiment, alignment of vertebrae of a spinal column is altered by attaching a first anchor to an upper vertebra and a second anchor to a lower vertebra as before. Then, two or more flexible tethers are connected to both the first anchor and the second anchor so each of the tethers spans between the upper vertebra and the lower vertebra. Although the tethers span adjacent vertebrae in one embodiment, it is contemplated that the tethers may span and be connected to non-adjacent vertebrae. It is further contemplated that the more than two anchors and/or more than two tethers may be used with this method.

As will be appreciated by those of ordinary skill in the art, the methods and systems described above are capable of correcting abnormal spinal curvatures without fusing vertebrae. Further, the methods and systems described above enable surgeons to modify spinal column alignment simultaneously in multiple directions. In other embodiments, it is envisioned that similar systems may be used to alter the alignment of other types of bones or bone fragments. In addition, the methods and systems described above are minimally invasive thereby reducing opportunity for complications during and following the surgical procedures. Those skilled in the art will appreciate that the methods and systems described above permit progressive adjustment of vertebrae or growth guidance, or modulation in the skeletally immature spine to obtain a desirable optimal alignment of the spinal column for the patient. By shaping the rods, tensioning the tethers and adjusting the rods or tether after the initial surgery, the surgeon may progressively affect the alignment and/or growth of the vertebrae.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions without departing from the scope of the invention, it is intended that all matter contained in the above description or shown in the accompanying drawings shall be interpreted as illustrative and not in a limiting sense.

What is claimed is:

1. A system for changing alignment of vertebrae of a spinal column, said system comprising:
a plurality of elongate members, each of said members having a length sufficient to span at least one pair of vertebrae in the spinal column; and
a plurality of anchors, each anchor including an elongate threaded shaft having a tip at one end adapted to enter bone and a head on the shaft at a position spaced from the tip, said head including a plurality of connector mounts spaced along the head, each of said mounts being adapted to connect one of said elongate members to the head; and
wherein a first of said elongate members is slidably engaged with a first of said connector mounts in a first of said anchors to permit sliding motion between said first elongate member and said first anchor; and
wherein a second of said elongate members is rigidly engaged with a second of said connector mounts in said first anchor to prevent sliding motion between said second elongate member and said first anchor, and wherein said second connector mount comprises a channel extending entirely through said head of said first anchor, and wherein said second elongate member is positioned within and extends entirely through said channel.

2. A system as set forth in claim 1 wherein said first of said elongate members comprises a flexible tether and said second of said elongate members comprises a rigid rod.

3. A system as set forth in claim 2 wherein said rigid rod has a circular cross section.

4. A system as set forth in claim 2 wherein the flexible tether comprises one of a synthetic ligament or a synthetic tendon.

5. A system as set forth in claim 2 wherein the flexible tether is formed of a polymeric material.

6. A system as set forth in claim 1 wherein one of said first and second elongate members has a first bending stiffness and another of said first and second elongate members has a second bending stiffness greater than said first bending stiffness.

7. A system as set forth in claim 6 wherein said first elongate member has said first bending stiffness and said second elongate member has said second bending stiffness.

8. A system as set forth in claim 1 wherein one of said first and second elongata members has a first tensile stiffness and another of said first and second elongate members has a second tensile stiffness greater than said first tensile stiffness.

9. A system as set forth in claim 8 wherein said first elongate member has said first tensile stiffness and said second elongate member has said second tensile stiffness.

10. A system as set forth in claim 1 further comprising a fastener operatively connected to said second connector mount and engaged with said second elongated member to fasten said second elongate member to said head of said first anchor.

11. A system as set forth in claim 1 wherein said elongate threaded shaft and said head of said first anchor are integrated to form a unitary single-piece structure.

12. A system as set forth in claim 1 wherein said channel is U-shaped; and
further comprising a threaded fastener operatively engaged within said U-shaped channel and engaged with said second elongated member to fasten said second elongate member to said head.

13. A system for changing alignment of vertebrae of a spinal column, said system comprising:
a plurality of elongate members, each of said members having a length sufficient to span at least one pair of vertebrae in the spinal column; and
a plurality of anchors, each anchor including an elongate threaded shaft having, a tip at one end adapted to enter bone and a head on the shaft at a position spaced from the tip, said head including a plurality of connector mounts spaced along the head, each of said mounts be adapted to connect one of said elongate members to the head; and
wherein a first of said elongate members is slidably engaged with a first of said connector mounts in a first of said anchors to permit sliding motion between said first elongate member and said first anchor; and
wherein a second of said elongate members is rigidly engaged with a second of said connector mounts in said first anchor to prevent sliding motion between said second elongate member and said first anchor; and
wherein each of said elongate members comprises a flexible tether comprising one of a synthetic ligament and a synthetic tendon.

14. A system for changing alignment of vertebrae of a spinal column, said system comprising:
a plurality of elongate members, each of said members having a length sufficient to span at least one pair of vertebrae in the spinal column; and
a plurality of anchors, each anchor including an elongate threaded shaft having a tip at one end adapted to enter bone and a head on the shaft at a position spaced from the tip, said head including a plurality of connector mounts spaced along the head, each of said mounts being adapted to connect one of said elongate members to the head; and
wherein at least one of said elongate members comprises a flexible tether and at least one of said elongate members comprises a rigid rod, and wherein the flexible tether comprises one of a synthetic ligament or a synthetic tendon.

15. A system as set forth in claim 14 wherein a first of said elongate members is slidably engaged with a first of said connector mounts in a first of said anchors to permit sliding motion between said first elongate member and said first anchor; and
wherein a second of said elongate members is rigidly engaged with a second of said connector mounts in said first anchor to prevent sliding motion between said second elongate member and said first anchor.

16. A system as set forth in claim 15 wherein said first of said elongate members comprises said flexible tether and said second of said elongate members comprises said rigid rod.

17. A method of changing alignment of vertebrae of a spinal column comprising:

attaching a first anchor to an upper vertebra;
attaching a second anchor to a lower vertebra; and
connecting at least two rods to both said first anchor and said second anchor so each of the rods spans between the upper vertebra and the lower vertebra; and
wherein a first of the rods is slidably engaged with the first anchor to permit sliding motion between the first rod and the first anchor; and
wherein a second of the rods is rigidly engaged with the first anchor to prevent sliding motion between the second rod and the first anchor, and wherein the flexible tether comprises one of a synthetic ligament or a synthetic tendon.

18. A method as set forth in claim 17 further comprising shaping the rods to guide vertebrae during spinal growth.

19. A method as set forth in claim 17 further comprising adjusting the rods to modulate spinal growth.

20. A method of changing alignment of vertebrae of a spinal column comprising:
attaching a first anchor to an upper vertebra;
attaching a second anchor to a lower vertebra;
connecting a rigid rod to both said first anchor and said second anchor so the rod spans between the upper vertebra and the lower vertebra; and
connecting a flexible tether to both said first anchor and said second anchor so the tether spans between the upper vertebra and the lower vertebra; and
wherein the flexible tether has a first bending stiffness and the rigid rod has a second bending stiffness greater than the first bending stiffness, and wherein the flexible tether comprises one of a synthetic ligament or a synthetic tendon.

21. A method as set forth in claim 20 further comprising shaping the rod to guide vertebrae during spinal growth.

22. A method as set forth in claim 20 further comprising adjusting at least one of the rod and the tether to modulate spinal growth.

23. A method as set forth in claim 20 wherein the flexible tether comprises one of a cable and a wire.

24. A system for changing alignment of vertebrae of a spinal column, said system comprising:
a plurality of elongate members, each of said members having a length sufficient to span at least one pair of vertebrae in the spinal column; and
a plurality of anchors, each anchor including an elongate threaded shaft having a tip at one end adapted to enter bone and a head on the shaft at a position spaced from the tip, said head including a plurality of connector mounts spaced along the head, each of said mounts being adapted to connect one of said elongate members to the head; and
wherein a first of said elongate members is slidably engaged with a first of said connector mounts in a first of said anchors to permit sliding motion between said first elongate member and said first anchor; and
wherein a second of said elongate members is rigidly engaged with a second of said connector mounts in said first anchor to prevent sliding motion between said second elongate member and said first anchor; and
a sleeve defining an opening with said first elongate member positioned within said opening and said sleeve engaged with said first anchor.

25. A system as set forth in claim 24 wherein said sleeve is clamped about said first elongate member to lock said sleeve in place on said first elongate member.

26. A system as set forth in claim 24 wherein said first connector mount comprises a passage extending through said head of said first anchor, and wherein said sleeve is engaged against an outer surface of said head of said first anchor adjacent said first connector mount.

27. A system for changing alignment of vertebrae of a spinal column, said system comprising:
   a plurality of elongate members, each of said members having a length sufficient to span at least one pair of vertebrae in the spinal column; and
   a plurality of anchors, each anchor including an elongate threaded shaft having a tip at one end adapted to enter bone and a head on the shaft at a position spaced from the tip, said head including a plurality of connector mounts spaced along the head, each of said mounts being adapted to connect one of said elongate members to the head; and
   wherein at least one of said elongate members comprises a flexible tether and at least one of said elongate members comprises a rigid rod; and
   wherein said flexible tether is selected from a group consisting of a wire, a cable, a filament, a fiber, a band, a mesh sheet, a ligament, and a tendon, and wherein said flexible tether comprises one of a synthetic ligament or a synthetic tendon.

28. A system for changing alignment of vertebrae of a spinal column, said system comprising:
   a plurality of elongate members, each of said members having a length sufficient to span at least one pair of vertebrae in the spinal column; and
   a plurality of anchors, each anchor including an elongate threaded shaft having a tip at one end adapted to enter bone and a head on the shaft at a position spaced from the tip, said head including a plurality of connector mounts spaced along the head, each of said mounts being adapted to connect one of said elongate members to the head; and
   wherein at least one of said elongate members comprises a flexible tether and at least one of said elongate members comprises a rigid rod, and wherein said flexible tether is formed of a polymeric material.

29. A system as set forth in claim 28 wherein said polymeric material comprises polyester.

30. A system as set forth in claim 28 wherein said rigid rod is formed of a metallic material.

31. A method of changing alignment of vertebrae of a spinal column comprising;
   attaching a first anchor to an upper vertebra;
   attaching a second anchor to a lower vertebra;
   connecting a rigid rod to both said first anchor and said second anchor so the rod spans between the upper vertebra and the lower vertebra; and
   connecting a flexible tether to both said first anchor and said second anchor so the tether spans between the upper vertebra and the lower vertebra; and
   wherein the flexible tether has a first bending stiffness and the rigid rod has a second bending stiffness greater than the first bending stiffness, and wherein the flexible tether is formed of a polymeric material.

32. A method as set forth in claim 31 wherein the rod is formed of a metallic material.

33. A system for changing alignment of vertebrae of a spinal column, said system comprising:
   a plurality of elongate members, each of said members having a length sufficient to span at least one pair of vertebrae in the spinal column; and
   a plurality of anchors, each anchor including an elongate threaded shaft having a tip at one end adapted to enter bone and a head on the shaft at a position spaced from the tip, said head including a plurality of connector mounts spaced alone the head, each of said mounts being adapted to connect one of said elongate members to the head; and
   wherein at least one of said elongate members comprises a flexible tether and at least one of said elongate members comprises a rigid rod; and
   a sleeve defining an opening with said flexible tether positioned within said opening and said sleeve engaged with said head of a corresponding one of said anchors.

* * * * *